United States Patent [19]

Hein et al.

[11] Patent Number: 4,759,755

[45] Date of Patent: Jul. 26, 1988

[54] DEVICE FOR TRANSFERRING LIQUID FROM A VIAL TO A MULTI-POINTED APPLICATOR

[75] Inventors: Gary L. Hein, Oakley; Donald R. Mowen, Decatur, both of Ill.

[73] Assignee: Lincoln Diagnostics, Inc., Decatur, Ill.

[21] Appl. No.: 929,756

[22] Filed: Nov. 12, 1966

Related U.S. Application Data

[63] Continuation of Ser. No. 708,211, Mar. 5, 1985, abandoned.

[51] Int. Cl.[4] ............................................. A61B 19/00
[52] U.S. Cl. ...................................... 604/403; 604/47; 604/295; 604/310; 604/407; 128/743; 222/420; 222/421
[58] Field of Search .................... 604/46, 47, 217, 251, 604/289, 290, 294–302, 310, 403, 407; 128/743; 222/420–422

[56] References Cited

U.S. PATENT DOCUMENTS

| Re. 19,520 | 4/1935 | Dykema | 604/295 |
| 688,544 | 12/1901 | Pitts | 604/295 |
| 1,985,703 | 12/1934 | Wheaton | 604/295 |
| 2,561,252 | 7/1951 | Waring | 604/289 |
| 2,800,253 | 7/1957 | Henderson | 604/298 |
| 3,289,670 | 12/1966 | Krug et al. | 128/743 |
| 3,325,059 | 6/1967 | Hein | 604/47 |
| 3,881,527 | 5/1975 | Shapiro | 222/420 |
| 4,237,906 | 12/1980 | Haustad et al. | 128/743 |

FOREIGN PATENT DOCUMENTS 1363517  5/1964  France ............... 222/420

Primary Examiner—C. Fred Rosenbaum
Assistant Examiner—Mario Costantino
Attorney, Agent, or Firm—Norman Lettvin; Fred S. Lockwood

[57] ABSTRACT

An elongated sleeve member having an upper open end and a lower open end, and with an annular flange extending radially outwardly from adjacent the open lower end is affixed to an elongated stem member in a substantially vertical orientation for immersion in a liquid substance held in a vial. A sleeve-like surface extending between the open ends of the elongated sleeve member, and a surface defining the lower end of the sleeve and an outwardly extending annular flange provide means to remove a consistent quantity of a liquid substance, such as a liquid allergenic agent, from a storage vessel or vial, and to transfer the liquid to a receiving scarifier structure, such as a cluster of multiple scarifier points. The outer periphery and upper surface of the flange provide a means for carrying excess liquid, and the flange provides for wiping the excess liquid from the sleeve member and flange prior to dispensing a desired quantity of liquid allergenic agent onto a cluster of scarifier points.

5 Claims, 1 Drawing Sheet

U.S. Patent　　　Jul. 26, 1988　　　4,759,755
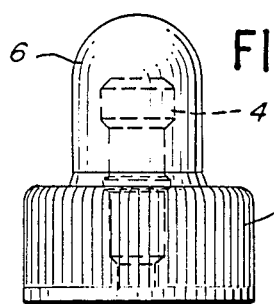
FIG. 1
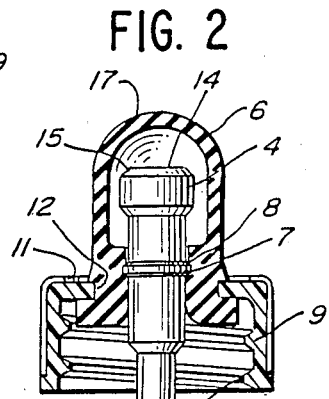
FIG. 2
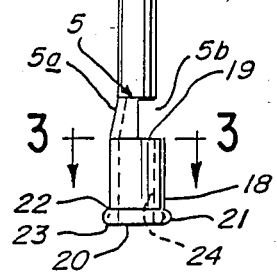
FIG. 3
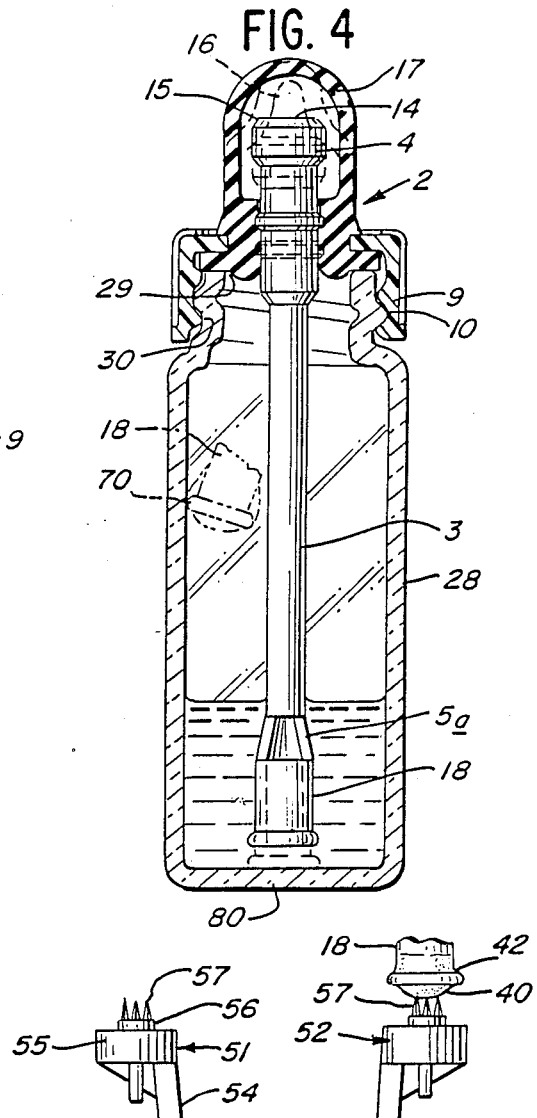
FIG. 4
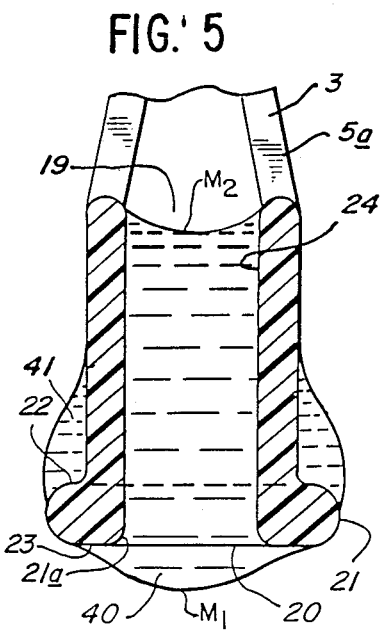
FIG. 5
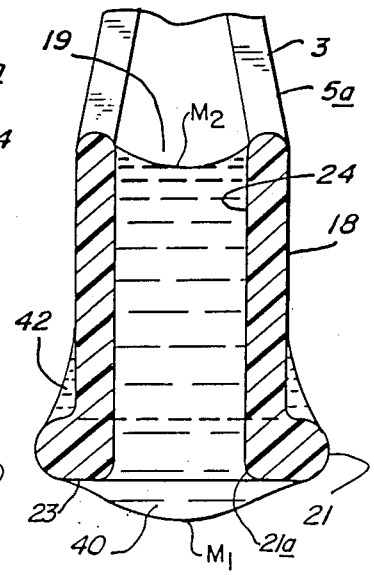
FIG. 6
FIG. 7
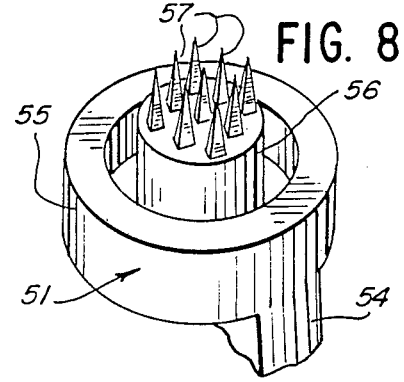
FIG. 8

DEVICE FOR TRANSFERRING LIQUID FROM A VIAL TO A MULTI-POINTED APPLICATOR

This is a continuation of application Ser. No. 708,211 filed Mar. 5, 1985 now abandoned.

BACKGROUND OF THE INVENTION

1. Field Of The Invention

This invention relates to a device for removing a quantity of a liquid substance, such as an allergenic agent, from a storage vessel and transferring said quantity of liquid to an application structure that is used to apply the allergenic agent to the skin.

2. Description of Prior Art

Application of a fixed, or consistent, quantity of an allergenic agent to an area of a patient's skin to evaluate the reactivity of the patient to the agent has long been a problem in allergy skin testing.

Devices for simultaneously applying a plurality of allergenic agents in liquid form to the human skin are known and are currently commercially available and used. One such device is disclosed in U.S. Pat. No. 3,556,080. The device disclosed in this patent has a plurality of antigen application heads. Each of the heads is engaged to a relatively rigid handle by a separate connective arm, and the arrangement is such as to enable all of the heads to simultaneously scarify, or penetrate, a separate area of skin on a non-planar portion of the body, such as on a patient's arm, leg or back. By placement of a different liquid allergenic agent on each head of the device of U.S. Pat. No. 3,556,080, the physician, or his technician, has available an instrument for simultaneously applying different allergenic materials, or concentrations of allergenic materials to multiple skin sites on the patient. The liquid allergenic agent is normally stored in small vials, and it is desirable that a proper amount of liquid allergenic agent be transferred from its storage vial to the scarifying head of the scarifying instrument.

Loading of a correct quantity of an allergenic agent on the cluster of scarifier or skin penetrating points of the heads of said instrument is important to obtain an accurate indication of the presence or absence of reactivity by the person being tested, and also to prevent waste of expensive allergenic agents.

Prior art constructions for loading a liquid agent onto multiple points of a scarifier head are disclosed in U.S. Pat. Nos. 3,325,059; 3,366,278; 3,369,708; 3,413,975; 3,465,717; and 3,552,605. These patents show use of devices purportedly for controllably applying a fixed amount of a liquid test substance to an application head, or by loading liquid by immersing the scarifying points of the head in a pool of the liquid substance. Such prior art constructions have not been widely adopted, because of lack of control insuring uniformity of transfer of a precise amount of liquid to the scarifying head.

Other approaches to the loading of the heads of the multiple test head applicator have included: using solid glass transfer rods which are dipped into a solution that includes the antigenic material and then deposit the liquid carried on the outside of the rod onto the points of a scarifier head; and use of an eyedropper which ingests, under squeeze bulb pressure, a quantity of liquid into a tubular glass sleeve for later discharge onto the points of the scarifier head. The liquid used as the antigen carrier is generally a mixture of 50% water and 50% glycerin.

With respect to the loading of the heads of the multiple test head applicator disclosed in the U.S. Pat. No. 3,556,080, various applicators have been tested. Solid glass rods having rounded ends and solid glass rods having bulbous enlargements formed on the application end have been found to transfer inconsistent quantities of liquid due to the varying degree to which they are immersed within the liquid and the inconsistent quantity of liquid which is withdrawn or "cleaned" from the rod when the rod contacts the side or mouth of the storage vessel.

Similarly, conventional dropper-type transfer devices provide inconsistent quantities as the quantity of substance transferred is dependent upon the amount of depression or "squeeze" of the rubber bulb of the stopper both when loading the stopper from the storage vessel and when unloading the stopper onto the test head.

Such devices, and approaches to the problem, have been found to be lacking precision because they are dependent upon the subjective judgment of the person using them and are prone to inconsistent cleaning or removal of some of the substance when intentionally or inadvertently placed in contact with other objects. Also, inconsistency promoting actions such as tapping the rod or stopper with a finger or abrupt up and down motions are often required to effect transfer of the substance from the device to the test head. All of these disadvantages make proper loading of a test head with a correct and consistent quantity of a liquid, that carries an allergenic agent, difficult, if not impossible, to attain.

SUMMARY OF THE INVENTION

An elongated member having a manually graspable upper end and an immersible lower end that is constructed and arranged to provide a vertically oriented open ended cylindrical sleeve member provides an efficient, easily manipulated device for holding and transferring consistent quantities of a liquid substance from a storage vessel, such as a bottle, to a receiving structure, such as a multiple point applicator head of an allergenic test device.

An annular flange extending radially outwardly from the lower open end of the cylindrical member serves to assure that a consistent quantity of liquid remains in the internal cylindrical end when a portion of the flange is touched against a portion of the storage vessel. Additionally, a lower surface of the flange and cylinder serves to shape the liquid substance carried by the cylindrical member for promoting desired transfer of the liquid to the receiving structure.

BRIEF DESCRIPTON OF THE DRAWINGS

FIG. 1 is an elevational view of a preferred embodiment of the liquid removal and transfer device of this invention;

FIG. 2 is a side elevation view of the removal and transfer device shown in FIG. 1, looking at the device from the right of FIG. 1, and in which the rubber vial cap, or stopper, is shown in an axial cross-sectional view;

FIG. 3 is an enlarged cross-sectional view of the device taken on section line 3—3 of FIG. 1;

FIG. 4 is an elevation view showing the device of FIG. 1 in its normal relationship to a liquid substance storage vessel and, also shows, by one set of phantom lines, the liquid carrying lower end of the device being "cleaned" of excess liquid by contact with an interior side of the vial, and further shows, by another set of phantom lines, the lowermost end of the transfer device being axially moved to the bottom of the vial;

FIG. 5 is an enlarged, fragmentary, sectional view of the immersible end portion of the removal and transfer device, showing a typical collection of a load of liquid substance on the lower end of the transfer device prior to "cleaning" of excess from the exterior thereof;

FIG. 6 shows the transfer device end seen in FIG. 5 after "cleaning" of excess liquid therefrom, and prior to transfer of the liquid substance to a receiving structure;

FIG. 7 is an end elevation view showing a typical allergenic agent application device having a plurality of liquid receiving test heads for receiving a liquid substance and applying it to a test area of skin, and showing illustratively the liquid carrying end of the transfer device in position for transferring a desired quantity of liquid to one of the test heads; and FIG. 8 is an enlarged perspective view of one of the test heads shown in FIG. 7 showing a typical cluster array of nine scarifying points for receiving and holding a quantity of liquid substance that has been transferred to the receiving structure by the device of this invention.

DETAILED DESCRIPTION OF THE PREFERRED EMBODIMENT

FIG. 1 shows a preferred form of a liquid removal and transfer device, generally designated at 2, and FIG. 2 shows the device 2 of FIG. 1 in another attitude with the upper portion sectioned for clarity.

The transfer device 2 includes an elongated stem member, or rod, 3 having a manually graspable upper portion 4 and a lower end portion, generally 5, that is adapted for immersion in liquid stored in a vial, as shown in FIG. 4. The upper end of upper portion 4 is provided and shaped, as shown, to enable manual handling or manipulation of the device. To facilitate handling, a resilient grip enhancing means, such as a conventional, molded, squeezable, bulb type stopper member 6, is preferably engaged with an upper portion of stem 3. A stopper member engagement means, such as an annular flange, or rib, 7 provided on stem 3, is located below upper stem portion 4, and is affixed to or formed integral with rod 3 and extends radially outward from the rod.

The flange 7 is received within an annular recess 8 formed in the resilient stopper member 6 to maintain the stopper member and the upper portion 4 of the rod 3 mutually engaged with each other. A substantially rigid, molded, closure means, such as annular cap 9, having a suitable securing means, such as internal helical threads 10, is provided for removable securing the stopper and rod assembly to the top opening or mouth of the vial or bottle used to store therein a liquid substance. The cap 9 and the resilient member 6 are mutually interengaged with each other by suitable means such as the annular flange 11 formed on the cap, and the provision of a flange-receiving annular recess 12 formed in the resilient member, substantially as shown in FIG. 2.

Upper end portion 4 of rod 3 has an upper terminal surface 14 surrounded by a downwardly diverging, or frustro-conical, portion, such as the downwardly and outwardly inclined, or curved, annular surface 15 which serves as a transition between terminal surface 14 and a cylindrical side surface of end portion 4. The terminal surface 14 and the adjacent frustro-conical portion 15 preferably are positioned in a substantial space or chamber 16 that is bounded by a relatively thin, flexible wall portion 17 of resilient member 6.

The lower, or immersible, end portion 5 of solid rod 3 is formed integrally with an axially elongated sleeve member 18, with an arcuate segment 5*a* connecting the upper end of sleeve member 18 with the lower end of rod 3, as seen in FIGS. 1, 2 and 3. The arcuate segment 5*a* provides a lateral opening 5*b* between the lower end of solid rod 3 and the upper end of a chamber surrounded by sleeve member 18.

Cylindrical member 18 has an upper open end 19, a lower open end 20, and an annular, outwardly extending, flange 21 formed on the exterior of member 18 adjacent the lower open end 20 thereof. Flange 21 extends radially outward from the outwardly facing cylindrical surface of member 18. An annular shoulder 22 is formed on the top surface, or upper end, of the flange 21, and an annular terminal surface 23 is formed at the lower surface, or bottom of the flange 21. The outer periphery of the flange 21 is preferably a convexly curved surface, as shown. The cylindrical member 18 provides thereon a cylindrical, axially elongated, inward facing surface 24 that extends between upper open end 19 and lower open end 20 of cylindrical sleeve member 18, thereby defining a cylindrical space which extends substantially the length of sleeve member 18. The lower end of the interior of cylindrical sleeve member 18 adjacent the lower flange is rounded, or bell shaped, at 21*a*. This interior bell shape of the sleeve facilitates loading of liquid material onto the points of an applicator as seen in FIG. 7 and reduces greatly any possibility of damaging the tips of the points during loading. The longitudinal axis of the space 24 is preferably formed substantially as a projected extension of the longitudinal axis of support rod 3 thereabove.

FIG. 4 shows the device 2 of this invention immersed in a pool of liquid substance in a storage vessel, such as a vial or bottle 28. Vial 28 has an opening 29 at its top. Opening 29 is preferably provided with appropriate means, such as threads 30, which are adapted to coact with the threads 10 on cap 9 to provide for sealed closure of vial 28.

The lower or immersible end 5 of rod 3 is sized to be easily passed through vial opening 29 to enable member 18 to be completely dipped into the liquid substance contained within vial 28, near the bottom of the vial. As shown in FIG. 4, the longitudinal length of rod 3 received within the vial is less than the axial length of the interior of the vial to normally preclude the member 18 from contacting the bottom of the vial.

However, due to the expense of the liquid allergenic substance stored in the vial, it is economic to maximize use of the liquid contained in each vial. To this end, the device 2 is designed to enable the user to extend the length or "reach" of rod 3 which extends into the vial 28. Placement of the thumb and a finger on substantially two diametrically opposed sides of the wall 17 of resilient member 6 and squeezing inward causes the interior portions of the walls which define space 16 to be forced against the frustro-conical surface portion 15 on stem 3 to cause rod 3 to be moved axially downwardly in vial 28. This squeezing action causes the rod 3 to be urged and moved downwardly with respect to the resilient member 6 and the substantially rigid cap member 9, to a postion as shown in phantom lines in FIG. 4 adjacent the bottom wall 80 of vial 28. This action enables the end 18 of rod 3 to be fully immersed in the smallest quantity of liquid remaining within vial 28. This extension of rod 3 maximizes usage of the contents of the vial.

FIG. 5 is an enlarged cross sectioned view of member 18 showing a typical configuration of the liquid substance clinging to the exterior and interior of member 18 after it has been immersed in the liquid and withdrawn from the liquid and prior to removal of excess liquid from the exterior of member 18.

As shown in FIG. 5, a quantity, or dosage, of liquid 40 is contained in space 24 with a lower meniscus $M_1$ that bulges downwardly, under gravity, and extends across lower open end 20 of member 18 and an upper meniscus $M_2$. The quantity of liquid load contained in dosage 40 is a function of the surface area of the inner surface 24 of sleeve 18 and the surface area of the annular lower surface 23 of the flange 21. It is this quantity of liquid which is desired to be removed from the vial for transfer onto a multiple point cluster as shown in FIGS. 7 and 8.

Additionally, an unwanted excess quantity of liquid 41 is normally picked up and rests on the top shoulder 22 of flange 21 and extends upwardly along the outer surface of sleeve 18. This excess liquid, if not removed prior to transfer of the liquid load to a receiving structure, may flow over the outer periphery of flange 21 and also be transferred to the receiving structure or overflow such receiving structure. Such an unwanted transfer to the cluster of points, or the structure surrounding or supporting such point cluster, causes the 'load' of liquid to break loose from the cluster of points and run down the sides and away from the tips of the points. This loading error causes unsatisfactory test results. Also, excessive dispensing, or use, of an excess quantity of liquid would be costly.

Therefore, and as best shown by FIG. 6, it is desirable to remove as much as possible of excess liquid 41 from sleeve 18 prior to removal of sleeve 18 from the vial. To accomplish such removal, or "cleaning", of excess liquid 41, the manipulator of device 2 only has to bring an edge portion of flange 21 into contact with an interior surface of the vial that is free of the pool of liquid in the vial, substantially as illustrated in phantom lines in FIG. 4. When contact is made as shown in the upper broken line view of FIG. 4, a quantity of liquid will be bled, or readily transferred, to the portion of the vial wall contacted, thus leaving a substantially lesser quantity of liquid 42 on and above flange 21 as shown in FIG. 6. The excess liquid that is bled off returns to the pool in the bottom of the vial and leaves a lesser amount of liquid both in the sleeve 18 and on the flange 21, as illustrated at 42 in FIG. 6. The size of the interior of sleeve 18 and of the flange 21 are selected so as to have the liquid quantity shown in FIG. 6 as the desired amount to be ultimately transferred to the scarifying cluster shown at 57 in FIGS. 7 and 8.

FIG. 7 shows by a fragmentary end view an allergenic agent applicator 50 having a plurality of test heads 51 and 52. One of the test heads is shown enlarged in FIG. 8. Applicator 50 may be formed having various numbers of test heads as disclosed in U.S. Pat. No. 3,556,080. A handle member 53, dimensioned to be substantially rigid, provides a means for manually grasping the assembly and also serves as part of the primary structural member.

Each test head is molded integrally with handle 53 and connects thereto by an attachment arm, such as arm 54. The attachment arms are preferably formed with a degree of flexibility to facilitate simultaneous application of a different allergenic agent on the skin of a non-planar portion of the body in one application of the applicator. As shown in phantom lines, an appropriate holding means 55 is normally used to hold the applicator in an inverted position for loading. In this position, a desired quantity of a different allergenic agent or biologic may be placed on each test head of applicator 50, using a number of devices 2 of this invention.

FIG. 8 is an enlarged perspective view of test head 51 shown in FIG. 7. Head 51 is comprised of an annular body member 55 having a centrally positioned cylindrical support member 56 extending outwardly of, or beyond, the extent of body member 55. Affixed to the top portion of support member 56 are a plurality of scarifier members 57. In one preferred form of test head, such as that shown in U.S. Pat. No. 3,556,080, nine such members are provided on each test head.

To load each test head using the device of this invention, the head is held in the inverted position shown in FIG. 7. One device 2 is unscrewed from engagement with its vial 28 and end 5 and member 18 are pulled upward above the level of liquid substance contained in the vial. A portion of flange 21 is then placed in contact with an interior wall portion of the vial, such as interior side portion 70 of the vial, as shown in phantom lines in FIG. 4, to remove excess liquid from the exterior of the member 18.

The liquid quantity 40 clinging to member 18, as seen in FIG. 6 is then placed in contact with the uppermost ends of scarifier members 57. As member 18 is moved downward to embrace the space that surrounds points 57, the quantity of liquid 40 on sleeve 18 will be transferred and flow, under gravity and capillary action, from sleeve 18 onto points 57 and into the interstices between the points 57. The quantity of liquid 42 will remain on member 18 and will be returned to the vial upon return of device 2 to its normal storage relationship with the vial.

As previously stated, the surface area of the surface defining the interior space of member 18, together with the surface area of the surface defining the lower terminal surface of the cylinder and of flange 21 determines the quantity of liquid that will be transferred to the scarifier members on the test head. The force of gravity causes the load 40 to bulge downwardly below the lower surface of sleeve 18, as seen in FIGS. 5 and 6.

In a preferred embodiment of the invention, a cylindrical sleeve member 18 having a length between open ends of 7 millimeters (0.280 inches) and an internal diameter of 3.1 millimeters (0.125 inches) with a lower flange member having an outside diameter of 5.8 millimeters (0.229 inches) was found to deposit an optimum quantity of liquid containing an allergenic agent onto a commercially available scarifier head, such as the one having nine scarifier members as seen in FIG. 8.

Elongated member 3 and cylindrical member 18 may be molded of a variety of moldable plastics, and in one embodiment were formed of injection molded polypropylene in which member 18, arcuate segment 5*a*, and rod 3 were molded as a single integral part. The quantity of substance removed from the vial and transferred preferably fills the interstitial spaces between the nine elongated pointed members 57 and wells laterally of and up to substantially the points or uppermost top ends of the members. A lesser quantity of substance will not cover all the surfaces of the points for ready and consistent transfer to a subject's skin. A greater quantity of liquid will have a tendency to flow off the members 57, thereby making application of an intended quantity of antigen difficult to control. Such an excess amount of antigen may provide a medically undesirable and economically wasteful deposit onto the skin of a subject.

While specific dimensions for a preferred embodiment of the loading sleeve 18 of the invention have been set out above, it will be understood that by changing the dimensions of the loading sleeve, the device may be adapted to accommodate liquid to be deposited where the liquid has different viscosity, or is being used at different temperatures. Therefore, and while the liquid that is to be used is normally 50% water and 50% glycerin, where those proportions change, the loading sleeve can be designed to accommodate all such variables to consistently provide for transfer of a preselected optimal quantity of a liquid.

The preferred embodiment as disclosed in the drawings and as described above performs well for its intended function. Also, a cylindrical member in which the lower open end is formed without a flange surrounding the lower open end will enable transfer of a fairly consistent load or dosage of liquid. In this somewhat less desirable alternate embodiment that does not have the flange surrounding the lower open end of the sleeve member, the removal or cleaning of excess material from the exterior surface of the cylindrical member by touching a portion of the exterior surface to another surface tends to be less effective and consistent and, consequently, the amount or load of liquid actually transferred to a receiving structure may tend to vary. For some applications or liquids, this variance in the amount of load transferred may be acceptable.

With the device of this invention a consistent quantity of a biologic testing substance can be consistently removed from its storage vial and be transferred to an applicator head to provide an optimum application, from both a medical and economic standpoint, of a dosage of the allergenic substance to the skin.

While one specific embodiment of our invention has been disclosed and described, the invention herein is to be interpreted as set out in the following claims.

What is claimed is:

1. A device for (1) withdrawing from a vial a sufficient quantity of a liquid agent to fully load a skin test head having a plurality of spaced scarifying points closely clustered to receive and retain thereon a predetermined load of withdrawn liquid agent, and (2) transferring said predetermined load of withdrawn liquid agent to said cluster of scarifying points, comprising:

an elongated rod-like member having attached to one end thereof one open end of a relatively short open-ended sleeve the other open end of which has an integrally formed bead-like flange means thereon;

said sleeve having a bore extending from end to end therethough large enough to fit down over said test head and completely encircle said cluster of spaced scarifying points; and, said bead-like flange means serving to (1) retain said liquid agent within said sleeve after said flange means has been brought into engagement with the interior surface of said vial so as to remove excess liquid from the exterior surface of said sleeve, (2) allow a portion of said withdrawn liquid agent to protrude downwardly below said bead-like flange means so as to be readily penetrated by said clustered scarifying points and (3) provide a guide in lowering said sleeve down over said test head.

2. The device called for in claim 1 wherein said vial is closed by removably closure cap means and the upper end of said rod-like member which is opposite said one end thereof to which said open-ended sleeve is attached is secured to said closure cap means.

3. The device called for in claim 2 wherein said closure cap means includes a protruding hollow resilient section, said upper end of said rod-like member extends into said resilient section, and said rod-like member is axially slidable in said cap means and may be forced to slide downwardly in said vial by applying force to said upper end thereof indirectly through said resilient section whereby said sleeve is moved closer to the bottom of said vial.

4. The method of transferring from a vial the quantity of liquid agent required to fully load without overloading a skin test head having a plurality of scarifying points closely clustered to receive and retain thereon a predetermined load of liquid agent, the steps which in sequence comprise:

dipping into the contents of a vial a small open-ended sleeve attached at one open end to a handle means and provided at its opposite end with a bead-like flange means and thereby taking up into said sleeve a quantity of liquid agent which equals approximately the maximum quantity of liquid agent said sleeve can retain;

lifting the loaded sleeve completely out of the liquid contents in said vial;

bringing said bead-like flange means into engagement with the interior surface of said vial at a level above the contents therein and thereby removing liquid agent that may be adhering to the exterior of said sleeve above said flange means which is in excess of that which will remain adherent after said engagement;

withdrawing said thus loaded sleeve from said vial;

lowering said loaded sleeve down and over said cluster of scarifying points on said test head whereby said points penetrate into said liquid agent; and lifting said sleeve from said test head and thereby transferring said predetermined load of liquid agent from said sleeve to said cluster of scarifying points.

5. The method of claim 4 wherein a residual quantity of said liquid agent remains with said sleeve when said sleeve is lifted from said test head.

* * * * *

UNITED STATES PATENT AND TRADEMARK OFFICE
CERTIFICATE OF CORRECTION

PATENT NO. : 4,759,755

DATED : July 26, 1988

INVENTOR(S) : Gary L. Hein, et al

It is certified that error appears in the above-identified patent and that said Letters Patent is hereby corrected as shown below:

On the title page, item [22] "Filed: Nov. 12, 1966" should read

--Filed: Nov. 12, 1986--.

Signed and Sealed this

Twenty-first Day of February, 1989

*Attest:*

DONALD J. QUIGG

*Attesting Officer*  *Commissioner of Patents and Trademarks*